United States Patent
Zunft

(10) Patent No.: US 6,412,351 B1
(45) Date of Patent: Jul. 2, 2002

(54) METHOD AND MEASURING APPARATUS FOR DETERMINING THE VOLUMETRIC GAS CONTENT

(75) Inventor: Stefan Zunft, Stuttgart (DE)

(73) Assignee: Deutsches Zentrum fuer Luft-und Raumfahrt e.V., Bonn (DE)

( * ) Notice: Subject to any disclaimer, the term of this patent is extended or adjusted under 35 U.S.C. 154(b) by 0 days.

(21) Appl. No.: 09/249,187

(22) Filed: Feb. 12, 1999

(30) Foreign Application Priority Data

Feb. 17, 1998 (DE) .......................................... 198 06 477

(51) Int. Cl.[7] .............................. G01F 1/74; G01N 7/00
(52) U.S. Cl. ............................. 73/861.04; 73/861.08; 73/19.01; 73/19.1
(58) Field of Search .................. 73/861.04, 861.08, 73/195, 861, 861.39, 861.49, 23.2, 29.01, 29.02, 335.04, 19.01, 19.1; 138/37, 38, 39, 44; 324/658, 684, 686, 688

(56) References Cited

U.S. PATENT DOCUMENTS

| | | | | |
|---|---|---|---|---|
| 1,689,446 A | * | 10/1928 | Miller et al. .................. | 138/37 |
| 3,421,077 A | * | 1/1969 | Liu et al. ..................... | 324/686 |
| 3,827,461 A | * | 8/1974 | Gilman ........................ | 138/37 |
| 3,938,967 A | * | 2/1976 | Reissmuller ................. | 138/37 |
| 4,713,603 A | * | 12/1987 | Thorn ......................... | 324/688 |
| 4,769,593 A | * | 9/1988 | Reed et al. .................. | 73/29.01 |
| 5,194,819 A | * | 3/1993 | Briefer ........................ | 324/684 |
| 5,361,632 A | * | 11/1994 | Magnani ..................... | 166/254.2 |
| 5,501,099 A | * | 3/1996 | Whorff ........................ | 73/861.04 |
| 5,563,518 A | * | 10/1996 | Durrett et al. .............. | 324/672 |
| 5,861,755 A | * | 1/1999 | Moerk et al. ................ | 324/663 |

FOREIGN PATENT DOCUMENTS

| | | |
|---|---|---|
| DE | 25 58 588 | 7/1977 |
| EP | 0 308 004 | 3/1989 |
| EP | 0 372 598 | 6/1990 |
| EP | 0 488 507 | 6/1992 |

OTHER PUBLICATIONS

Use of Breakup time data and velocity history data to predict the maximum size of stable fragments for acceration-induced breakup of a liquid drop. vol. 13, pp. 741–757, Jan. 1987.*

Measurement of void fraction in steam-generating solar collectors using a capacitance sensor, pp. 26–28, Jun. 2001.*

* cited by examiner

Primary Examiner—Harshad Patel
(74) Attorney, Agent, or Firm—Barry R. Lipsitz

(57) ABSTRACT

A method and apparatus for determining the volumetric gas content in a two-phase flow of a medium comprising a gas phase and a liquid phase which has an unknown flow shape are provided. Simple and reliable measurements are achieved by converting the two-phase flow into a droplet flow by vortexing the gas phase and the liquid phase, such that the determination of the volumetric gas content may be carried out in the droplet flow.

18 Claims, 2 Drawing Sheets

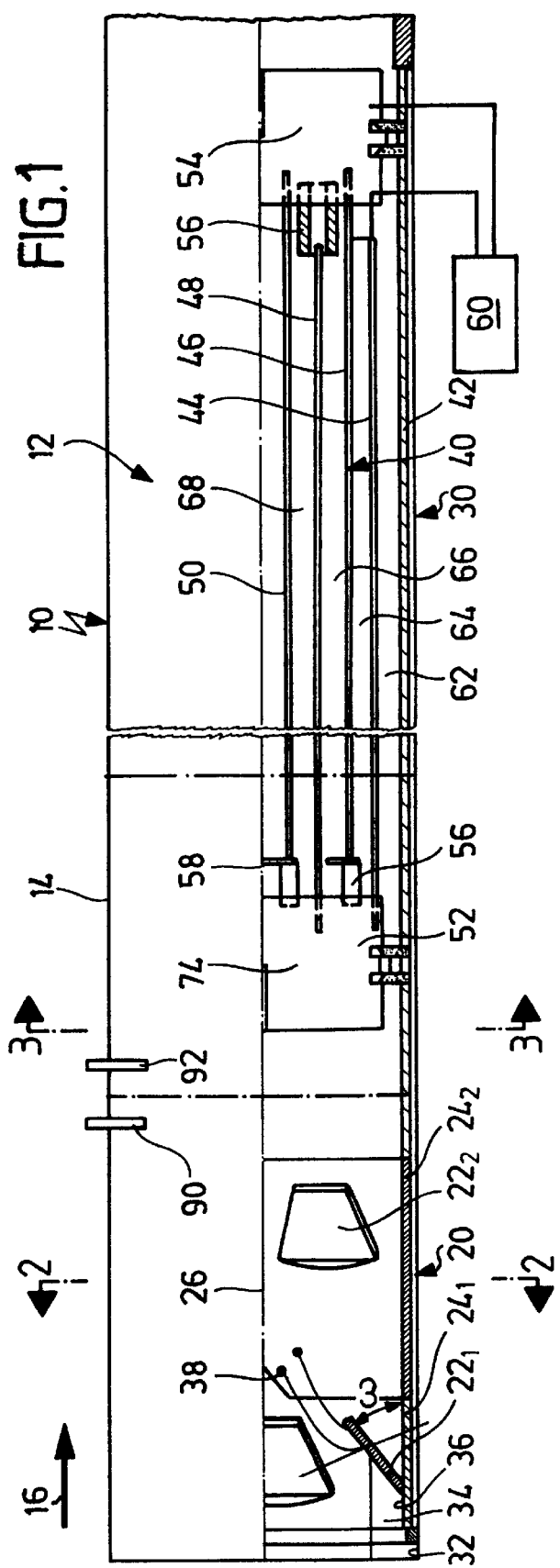

METHOD AND MEASURING APPARATUS FOR DETERMINING THE VOLUMETRIC GAS CONTENT

The present disclosure relates to the subject matter disclosed in German patent application No. 198 06 477.2 of Feb. 17, 1998, the entire specification of which is incorporated herein by reference.

BACKGROUND OF THE INVENTION

The invention relates to a method and a measuring apparatus for determining the volumetric gas content in a two-phase flow of a medium comprising a gas phase and a liquid phase and having an unknown flow shape.

In a large number of cases in process technology, for example, in power plant technology, it is necessary to determine the volumetric gas content in two-phase flows.

Where two-phase flows comprising water and steam are very often used, particularly in power plant technology, it is important to be able to determine the volumetric steam content of this two-phase flow exactly.

The methods known to date are based on the absorption or scattering of radioactive radiation such as, for example, γ-radiation, X-ray radiation or neutron radiation. However, impedance methods, for example, methods for measuring capacitance are also known, these being advantageous as far as their apparatus expenditure and their speed of response are concerned, but harboring considerable measurement inaccuracies owing to the unknown flow shape of the two-phase flow.

All of the methods known to date do, however, have in common the problem that the unknown flow shape which cannot be ascertained in a meaningful way, i.e., the unknown local distribution of the liquid phase relative to the gas phase, has a significant influence on the measurement results and so the measurement results always contain considerable errors.

SUMMARY OF THE INVENTION

The object underlying the invention is, therefore, to provide a method and a measuring apparatus with which measurements which are as reliable as possible can be carried out with a measuring technique which is as simple as possible.

This object is accomplished in a method of the kind described at the outset, in accordance with the invention, in that the two-phase flow is converted into a droplet flow by vortexing the gas phase and the liquid phase, and in that the volumetric gas content is determined in the droplet flow.

The advantage of the solution according to the invention is to be seen in that the two-phase flow with an unknown flow shape of the gas phase and the liquid phase is converted into a two-phase flow in the form of a droplet flow and with this droplet flow it is then possible to determine the volumetric gas content in a simple way as the unknown flow shape has been converted into a known flow shape, namely the droplet flow.

In accordance with the invention, a defined flow shape is thus generated in a compulsory way. Furthermore, with the droplet flow, an essentially homogeneous distribution of the liquid phase in the gas phase can be assumed for the determination of the volumetric gas content and so all inaccuracies arising from the unknown flow shape which, to date, has constituted a problem, are eliminated, and a simple model connection—for example, a quasihomogeneous model—exists between the directly measured quantity and the volumetric gas content.

On the other hand, the droplet flow has the advantage that it can be assumed that the slip, i.e., the quotient of the velocity of the gas phase and the velocity of the liquid phase can be set at approximately one, as the droplets move at the same speed as the gas phase in the direction of flow. Thus, a computational connection can be established with the gas content of the flow, which is often sought in practice and is related to the mass flow, without empirical and mostly quite rough slip models being required.

With the solution according to the invention, it is, in principle, conceivable to determine the volumetric gas content as before with a method based on absorption or scattering of radioactive radiation. The inventive solution would also prove advantageous for such a measurement in view of the no longer prevailing slip and the homogeneous distribution of the liquid phase in the gas phase.

However, a particularly expedient solution makes provision for the volumetric gas content to be determined by measuring capacitance. The measuring of capacitance has the advantage that the apparatus of the measuring arrangement is simple in comparison with methods which work with absorption or scattering of radioactive radiation. Capacitance measurement has the further advantage that in the case of the droplet flow used in accordance with the invention quasihomogeneous models for an effective relative permittivity of the two-phase dielectric can be used in order to establish the connection between the measured capacitor capacitance and the volumetric gas content or steam content of the two-phase flow.

Furthermore, a particularly expedient solution makes provision for the effective relative permittivity of more than half of the entire droplet flow to be determined for measuring the capacitance, i.e., more than half of the droplet flow is detected when measuring the capacitance, and, consequently, in contrast to the methods working with absorption or scattering of radioactive radiation, a substantial portion of the droplet flow is taken into consideration.

It is even more advantageous for essentially the entire droplet flow to be used for measuring the capacitance so that even inhomogeneities still prevailing in the droplet flow can be averaged by considering essentially the entire droplet flow.

In principle, the capacitance measurement could be carried out using a capacitance measuring arrangement in which the droplet flow permeates an electric field of a capacitor arrangement.

A better solution as regards the measuring technique does, however, make provision for the droplet flow to be divided up into portions and for the portions to each be passed through a respective capacitor.

The capacitors could, for example, be arranged such that the field lines thereof all run essentially parallel, i.e., the several capacitors would be stacked in layers. It is, however, particularly expedient for the capacitors to have fields extending radially in relation to a center axis and to be built up of annular electrodes.

A particularly expedient capacitance measuring arrangement makes provision for the capacitors to be formed by a set of annular electrodes arranged one within the other, each with a progressively smaller radius, which thus form a set of annular spaces through which the two-phase flow can then pass in the direction parallel to a center axis.

So far no details of the generation of the droplet flow have been given in the explanation of the various embodiments.

An advantageous embodiment makes provision for a mixer to be used for generating the droplet flow.

Such a mixer is preferably designed such that the liquid phase is broken up into droplets by flow guide blades therein. These flow guide blades preferably deflect in the direction of a center axis a flow of the liquid phase located at the edges and surrounding the gas phase at least partially and hence break it up into droplets.

Furthermore, the object stated at the outset is accomplished with a measuring apparatus for determining the volumetric gas content in a two-phase flow of a medium comprising a gas phase and a liquid phase and having an unknown flow shape, in accordance with the invention, in that the measuring apparatus comprises a mixer which converts the two-phase flow into a droplet flow by vortexing the gas phase and the liquid phase, and in that a measuring arrangement for determining the volumetric gas content of the droplet flow is arranged so as to follow the mixer.

Herein it is particularly advantageous for the measuring arrangement to comprise a capacitance measuring arrangement with which an effective relative permittivity of the droplet flow representing a two-phase dielectric can be measured.

A particularly expedient solution makes provision for the capacitance measuring arrangement to be arranged such that more than half of the droplet flow flows through this capacitance measuring arrangement.

It is even better for the entire droplet flow to flow through the capacitance measuring arrangement.

It is particularly expedient for the configuration of the capacitance measuring arrangement to be such that the capacitance measuring arrangement comprises not only one capacitor but several capacitors connected in parallel, and for different portions of the droplet flow to each flow through one of the capacitors.

Widely varying configurations are conceivable for the arrangement of the fields in such capacitors. For example, a layer construction is conceivable so the field lines of the individual capacitors run essentially parallel to one another.

A more advantageous solution makes provision for the capacitors to be formed by a set of annular electrodes arranged one following the other in a radial direction in relation to a center axis.

An expedient solution makes provision for the annular electrodes arranged one following the other to have a successively smaller radius and for all of the annular electrodes to be arranged coaxially with-the center axis.

Furthermore, in order that they will have as large a capacitance as possible, the annular electrodes are designed so as to extend over as large a distance as possible in the direction of flow and so the annular electrodes are preferably in the form of tubular cylinders which sit one in the other.

The individual annular electrodes are expediently connected to one another such that these form capacitors connected in parallel, and the entire capacitance of all capacitors can thus be used for measuring the effective relative permittivity of the droplet flow.

An expedient solution for achieving this makes provision for next annular electrodes but one to be connected so the total number of the annular electrodes can be operated such that the one amount of next annular electrodes but one which are electrically connected to one another is connected to ground and the other to a measuring potential.

It is, however, also conceivable to form two capacitor arrangements arranged one following the other in the direction of flow, and for the two capacitor arrangements to be operated in a push-pull circuit.

The advantage of such a push-pull circuit is to be seen in that interferences, in particular, the influences of magnetic interference fields are compensated.

The two capacitor arrangements are preferably likewise formed by sets of annular electrodes, and the same portions of the droplet flow always flow through capacitors corresponding to one another.

So far, the explanation of the various embodiments has also not given any details of the construction of the mixer. An advantageous embodiment makes provision for the mixer to have flow guide blades which preferably detach a liquid phase flowing at the edges of a channel and accelerate it in the direction of the center axis and create vortexes in order to break the liquid phase up into droplets by momentum exchange between the phases.

As an alternative or supplement thereto, a two-phase flow can also be converted into a droplet flow by a cross-sectional constriction, in particular, a venturi nozzle, and an improved momentum exchange and hence an improved vortexing are achievable by the increase in the flow velocity.

A particularly expedient solution could even make provision for arranging the inventive measuring arrangement in the area of a cross-sectional constriction and hence operating in the measuring arrangement with a flow velocity which is increased in comparison with a conventional channel or pipe cross section for the two-phase flow.

The flow guide blades are preferably in the form of portions bent out of a channel insert. It is, for example, conceivable to construct the channel insert as an insertion pipe carrying the flow guide blades.

Further features and advantages of the inventive solution are the subject of the following description and the drawings of several embodiments.

BRIEF DESCRIPTION OF THE DRAWINGS

FIG. 1 a side view of a first embodiment of an inventive measuring apparatus, a half side of which is shown in section;

FIG. 2 a section along line 2—2 in FIG. 1;

FIG. 3 a section along line 3—3 in FIG. 1;

DETAILED DESCRIPTION OF THE INVENTION

Figure 4:
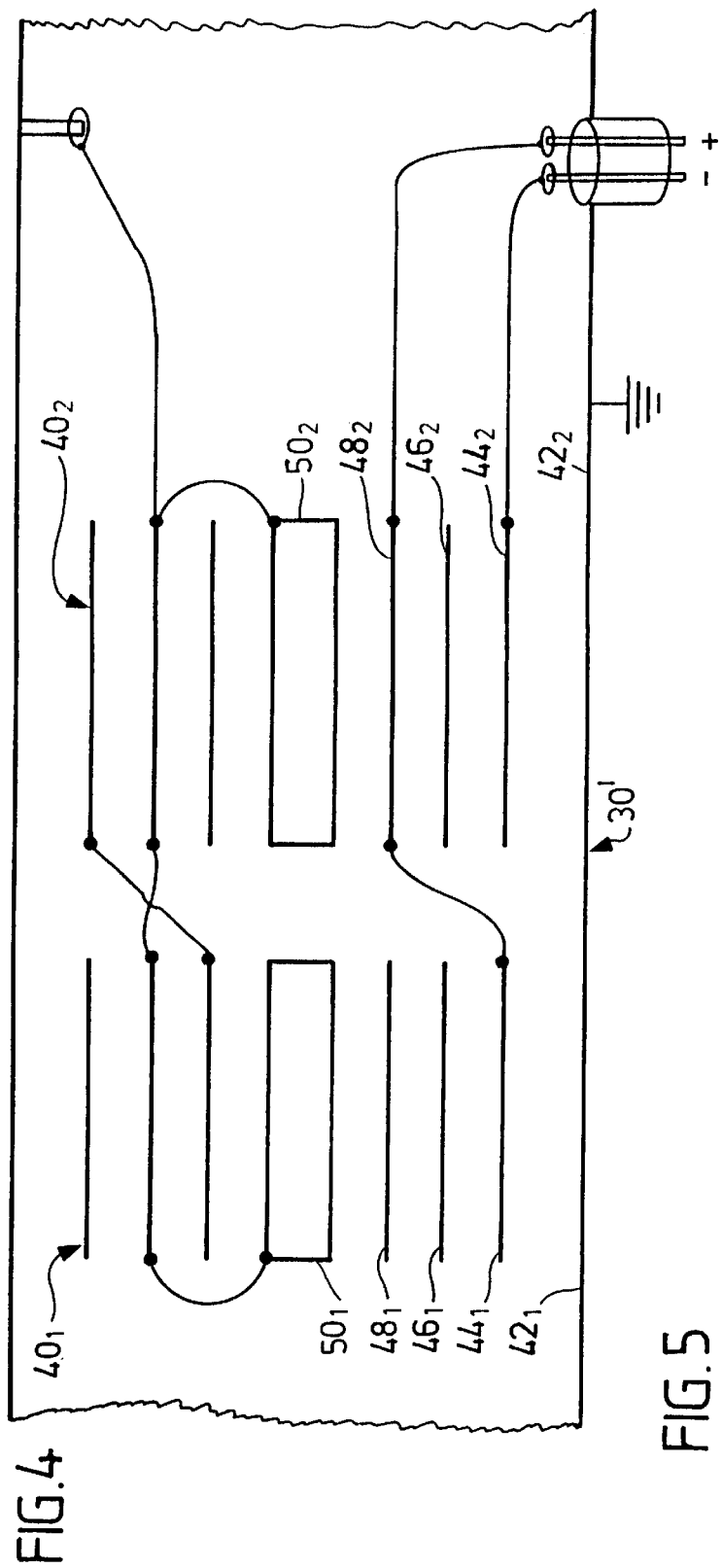
FIG. 4 an enlarged section similar to FIG. 1 through a capacitance measuring arrangement of a second embodiment of an inventive measuring apparatus.

A first embodiment of a measuring apparatus according to the invention generally designated 10 in FIG. 1 comprises a flow channel 12 formed, for example, by an inner channel of a pipe 14 in which a two-phase flow containing a gas phase and a liquid phase of a medium, for example, water and steam of a steam generator, flows in a direction of flow 16.

The measuring apparatus comprises a mixer generally designated 20 and a capacitance measuring arrangement generally designated 30 arranged downstream from the mixer.

The mixer 20 is formed by flow guide blades 22 which are held, for example, on an insert 24 as sheet metal segments projecting at an angle ω inwards in the direction of a center axis 26 of the pipe 14. The sheet metal segments extend approximately over more than a third of the radius of the pipe 14 in the direction of the center axis 26 so their inside edges 28 lie closer to the center axis 26.

Two sets of flow guide blades $22_1$ and $22_2$ arranged one following the other in the direction of flow and both projecting radially inwardly from an insert $24_1$ and $24_2$ respectively, are preferably provided. The two sets of flow guide blades $22_1$ and $22_2$ are rotated with respect to each other.

These flow guide blades 22 serve to detach a liquid phase 34 moving along an inside wall 32 of the pipe 14 in the direction of flow 16, in particular, from an inside wall 36 of the insert 24, and accelerate it in the direction of the center axis 26 and generate vortexes so that the liquid phase 34 flowing initially at least partially coherently is atomized into single drops 38 by momentum exchange between the phases.

The two-phase flow thus exits from the mixer 20 as droplet flow and enters as such the capacitance measuring arrangement 30.

In the simplest case of the first embodiment, the capacitance measuring arrangement 30 comprises a set 40 of annular electrodes extending around the center axis 26, with a first annular electrode 42 forming an outer pipe resting against the inner side 32 of the pipe 14, and the second annular electrode 44, the third annular electrode 46, the fourth annular electrode 48 and the fifth annular electrode 50 each being in the form of a tubular cylinder held with its upstream and downstream ends in holders 52 and 54, respectively, and centered therein in relation to the center axis 26.

The holders 52 and 54 simultaneously serve to contact the single annular electrodes 42 to 50, with, for example, the holder 52 electrically connecting the second annular electrode 44 and the fourth annular electrode 48 to each other, while the holder 54 connects the first annular electrode 42, the third annular electrode 46 and the fifth annular electrode 50 electrically to each other, for example, in the simplest case, by the holder 52 and 54, respectively, being electrically conductive and the respective annular electrode to be contacted being electrically conductively connected to the respective holder 52 or 54, whereas the annular electrode not to be contacted is connected via an insulator 56 to the respective holder 52 or 54, and is thus held thereon.

Furthermore, the fifth annular electrode 50, which is also in the form of a tubular cylinder, is closed at its front end, i.e., at its upstream end by a cover 58 so the entire two-phase flow passing as droplet flow through the capacitance measuring arrangement 30 is forced to flow through between the first annular electrode 42 and the fifth annular electrode 50 and thus permeate the electric fields forming between these with field lines running radially in relation to the center axis 26.

A capacitance measuring device 60 whose one output is connected, for example, to the second annular electrode 44, and whose other output is electrically conductively connected to the holder 54 and hence to the first annular electrode 42, the third annular electrode 46 and the fifth annular electrode 50, thus generates in successive spaces 62, 64, 66, 68 between the first annular electrode 42 and the second annular electrode 44, the second annular electrode 44 and the third annular electrode 46, the third annular electrode 46 and the fourth annular electrode 48 and between the fourth annular electrode 48 and the fifth annular electrode 50 alternately oppositely directed electric fields, which, however, belong to fields of capacitors connected in parallel.

If, for example, the first space 62 is allocated to a first capacitor, then the second space 64 is allocated to a second capacitor, the third space 66 to a third capacitor, and the fourth space 68 to a fourth capacitor, and their capacitance is simultaneously measured by the capacitance measuring device 60.

Owing to the fact that the fifth annular electrode 50 is closed by the cover 58, the entire droplet flow is forced to pass through the spaces 62 to 66 and hence the entire capacitance measuring arrangement 30 and so the effective permittivity and hence the proportion of droplets in the entire droplet flow can be determined by measurement of the capacitance with the capacitance measuring device 60.

The holders 52 and 54 are preferably of such design that, as shown in FIG. 3, they each have two plates 70 and 72 which extend with their respective flat side 74 parallel to the direction of flow 16 and include approximately a right angle between them and, in addition, extend in the radial direction in relation to the center axis 26. The plates 70 and 72 are preferably held in the area of their outer ends 76 and 78 by insulators 80 and 82 in the outer pipe forming the first annular electrode 42 and are thus also electrically insulated therefrom so that an electrically conductive connection can be made in an unproblematic way between the second annular electrode 44 and the fourth annular electrode 48.

The holder 54 is designed in the same way, and it is likewise held by insulators in the outer pipe 42, and an electric contact is made between the first annular electrode 42, the third annular electrode 46 and the fifth annular electrode 50 via an additional electrically conductive connection.

To determine the volumetric gas content of the two-phase flow in accordance with the invention, a temperature of the droplet flow is preferably determined by means of a temperature sensor 90 and a pressure thereof by means of a pressure sensor 92. By determining the capacitance of the capacitance measuring arrangement 30 by means of the capacitance measuring device 60, a determination of the volumetric gas content α of the two-phase flow is possible, as described in the article by H. Auracher, "Die Genauigkeit kapazitiver Verfahren zur Messung des volumetrischen Dampfgehalts in Zweiphasenströmungen" in the periodical "Wärme- und Stoffübertragung 21", pages 355 to 366 (1987). The volumetric gas content represents the relationship of the cross-sectional area through which the gas phase flows to the area of the entire flow cross section.

Proceeding from the fact that on account of the droplet flow the slip in the two-phase flow between the liquid phase and the gas phase is approximately equal to 1, the relationship between the gas mass flow component $\dot{X}$ and the volumetric gas content α is as follows:

$$1 = \frac{\dot{x}}{1-\dot{x}} \cdot \frac{1-\alpha}{\alpha} \cdot \frac{\rho_{fl}}{\rho_{gas}}.$$

The gas content of the two-phase flow which is related to the mass flow can thus be determined in an unproblematic way from this relationship.

Figure 5:
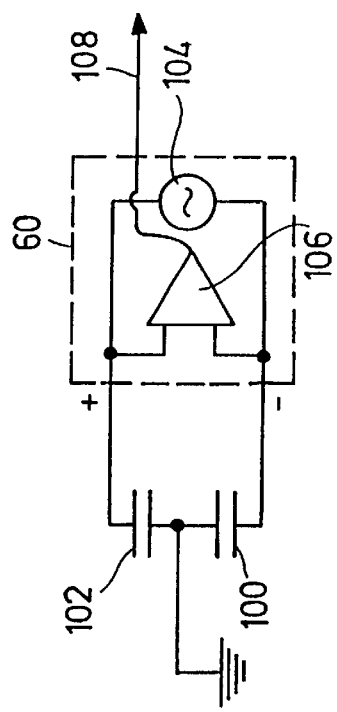
FIG. 5 a circuit plan of the capacitance measuring arrangement of the second embodiment.

In a second embodiment of a measuring device according to the invention for determining the volumetric gas content, shown in FIGS. 4 and 5, the mixer 20 is identical in design to that of the first embodiment.

However, the capacitance measuring arrangement 30' is of different design insofar as it comprises two sets $40_1$ and $40_2$ of annular electrodes, and these annular electrodes are connected to one another so as to form two capacitor arrangements 100 and 102 operated in push-pull relation to one another (FIG. 5).

For example, opposite the annular electrodes $42_1$, $42_2$, $46_1$, $46_2$ and $50_1$, $50_2$, connected to ground, the annular electrodes $44_2$ and $48_1$ are connected to a negative potential (−) and form with the annular electrodes connected to ground the first capacitor arrangement 100, while the annular electrodes $48_2$ and $44_1$ are connected to a positive potential (+) and thus form with the annular electrodes connected to ground the second capacitor arrangement 102. As will be apparent from the circuit diagram in FIG. 5, the two electrode arrangements 100 and 102 are connected and operated in push-pull connection. The capacitance measuring device 60 comprises, for example, an a.c. voltage source 104 and a measurement amplifier 106 which measures the voltage between the connection of the capacitor arrangement 100 connected to negative potential (−) and the connection of the capacitor arrangement 102 connected to positive potential (+) and delivers via an output line 108 a signal corresponding to the capacitance of the capacitor arrangements 100, 102.

Owing to the push-pull connection of the two capacitor arrangements 100 and 102, a measuring technique which is improved with respect to susceptibility to interferences and allows a more precise measurement of the capacitance is now made available.

Aside from that, however, the second embodiment operates in exactly the same way as the first embodiment. Therefore, reference is to be had in full to the description of the first embodiment for details of the other components.

What is claimed is:

1. A method of determining volumetric gas content in a two-phase flow of a medium comprising a gas phase and a liquid phase, said two-phase flow having an unknown flow shape, comprising the steps of:
   converting the two-phase flow into a droplet flow by vortexing the gas phase and the liquid phase; and
   determining the volumetric gas content in the droplet flow.

2. A method in accordance with claim 1, wherein said determining step comprises measuring capacitance.

3. A method in accordance with claim 2, further comprising the steps of:
   dividing the droplet flow into portions; and
   passing the portions of the droplet flow through a respective capacitor.

4. A method in accordance with claim 2, wherein an effective relative permittivity of more than half of said droplet flow is determined when measuring said capacitance.

5. A method in accordance with claim 2, wherein an effective relative permittivity of substantially all of said droplet flow is determined when measuring said capacitance.

6. A method in accordance with claim 1, wherein a mixer is used to convert the two-phase flow into the droplet flow.

7. A method in accordance with claim 6, wherein said liquid phase is broken up into droplets by flow guide blades in said mixer.

8. Apparatus for determining volumetric gas content in a two-phase flow of a medium comprising a gas phase and a liquid phase, said two-phase flow having an unknown flow shape, said apparatus comprising:
   a mixer for converting the two-phase flow into a droplet flow by vortexing the gas phase and the liquid phase,
   said mixer having flow guide blades which accelerate the liquid phase in a direction of a center axis such that the liquid phase is broken up into droplets having a flow from which said volumetric gas content can be determined.

9. Apparatus in accordance with claim 8, wherein said volumetric gas content is determined using a capacitance measuring arrangement for measuring an effective relative permittivity of the droplet flow representing a two-phase dielectric.

10. Apparatus in accordance with claim 9, wherein more than half of the droplet flow flows through the capacitance measuring arrangement.

11. Apparatus in accordance with claim 9, wherein substantially all of the droplet flow flows through the capacitance measuring arrangement.

12. Apparatus in accordance with claim 9, wherein;
   said capacitance measuring arrangement comprises several capacitors connected in parallel;
   the droplet flow is divided into portions; and
   each portion of the droplet flow is passed through a respective capacitor.

13. Apparatus in accordance with claim 12, wherein said capacitors are formed by a set of individual annular electrodes arranged sequentially in a radial direction in relation to the center axis.

14. Apparatus in accordance with claim 13, wherein;
   said sequentially arranged annular electrodes are arranged coaxially with the center axis; and
   each of said sequentially arranged annular electrodes has a successively smaller radius.

15. Apparatus in accordance with claim 13, wherein said annular electrodes comprise tubular cylinders.

16. Apparatus in accordance with claim 13, wherein the individual annular electrodes are connected to one another to form said-capacitors connected in parallel.

17. Apparatus in accordance with claim 9, wherein:
   the capacitance measuring arrangement comprises a push-pull circuit containing two capacitor arrangements arranged sequentially in a direction of flow.

18. Apparatus in accordance with claim 8, further comprising;
   a channel insert, wherein said flow guide blades are formed from portions of the channel insert bent outward.

* * * * *